United States Patent [19]

Landau

[11] 4,266,541

[45] May 12, 1981

[54] PRESSURE HYPODERMIC INJECTOR FOR INTERMITTENT VACCINATION

[75] Inventor: Sergio Landau, Rio de Janeiro, Brazil

[73] Assignee: Halen-Elliot do Brazil Industria e Comercio Equipamentos de Precisao Ltda., Rio de Janeiro, Brazil

[21] Appl. No.: 76,456

[22] Filed: Sep. 17, 1979

[30] Foreign Application Priority Data

Apr. 26, 1979 [BR] Brazil ................................. 780153

[51] Int. Cl.³ .............................................. A61M 5/00
[52] U.S. Cl. ........................... 128/207.23; 128/218 A
[58] Field of Search ................... 128/218 R, 215, 216, 128/207.23, 207.25, 218 A, 218 D, 218 DA

[56] References Cited

U.S. PATENT DOCUMENTS

| 3,057,349 | 10/1962 | Ismach | 128/207.23 |
| 3,526,225 | 9/1970 | Isobe | 128/207.23 |
| 3,908,651 | 9/1975 | Fudge | 128/207.23 |
| 4,059,107 | 11/1977 | Iriguchi et al. | 128/207.23 |

*Primary Examiner*—John D. Yasko
*Attorney, Agent, or Firm*—Emory L. Groff, Jr.

[57] ABSTRACT

A pressure liquid injector, for purposes of immunization includes one part in the shape of a pistol which houses the oil-hydraulic assembly for storage of energy and another part which comprises the vaccine suction and injection assembly. These two assemblies may be quickly connected and disconnected one from the other without permitting entrance of air into either of the two systems, particularly into the ducts and places where the vaccine is circulated and stored. Thus, a number of vaccine assemblies can be kept in a refrigerator and used one at a time in conjunction with the same hydraulic assembly, according to the need for application.

5 Claims, 2 Drawing Figures

VIEW A

PRESSURE HYPODERMIC INJECTOR FOR INTERMITTENT VACCINATION

This invention relates to an injector of liquid under pressure for purposes of immunization, with the particular advantage that the liquid suction and injection assembly may at any time be quickly disconnected from the oil-hydraulic assembly for storage of energy, without entrance of air into the two systems. This feature makes it possible to use the apparatus intermittently in places where vaccines are routinely applied, or any other type of subcutaneous or intradermic injection, since it is necessary to keep the vaccine at a low temperature and consequently to transfer it repeatedly from the injector to the refrigerator.

All other hypodermic injectors of which I am aware which are capable of administering 1 cc of liquid under high pressure have been designed for the specific purpose of being used in mass vaccination, that is, vaccination requiring a minimum number of applications per hour, since otherwise the vial of vaccine placed in the injector would lose its immunizing properties due to the surrounding temperature. Naturally, when the number of applications per hour is very high the vaccine in the vial placed in the injector is used up rapidly, and therefore does not lose its properties because of the high temperature. However, when applications are few and the same vial of vaccine (generally 50 cc) lasts more than an hour, it has to be removed from the injector and stored in a refrigerator, since otherwise the vaccine would lose its potency.

Since the injectors existing on the market were designed for the case of mass vaccination, where the patients generally wait in line to be vaccinated no thought was given to the possibilty of having to remove the vial from the injector before its content was used up. Consequently, upon removal of the vial, the system loses the necessary seal and air is permitted to enter, so that the jet of vaccine tends to form a spray. In other words, every time the vial is removed from the apparatus a small amount of air enters the vaccine suction and injection system, forcing the operator, after putting back the vial, to waste the first few doses in order to get rid of the air. Furthermore, it is also to be recommended that the vaccinator sterilize part of the suction and injection assembly upon removing the vial from the injector, since the contact of atmospheric air especially with the point of the cannula by which the vaccine is aspirated, is highly prejudicial to the sterility necessary to this system.

The result is that use of mass vaccination injectors loses its practical character completely when it is a question of routine vaccination, since the work of the operator in removing and replacing the same vial a number of times to keep the vaccine chilled is much greater than the work of vaccinating with individual syringes. In this case, consequently, the latter are widely preferred to pressure injectors.

It was therefore necessary to create an apparatus for injection under pressure that, while saving the work of individual sterilizations, should also avoid waste of the immunizing liquid during intermittent vaccination. That is, it should be an apparatus which, whether used successively for hours or intermittently for occasional injections, would give exactly the same performance, without causing any additional work to the vaccinator or any systematic waste of vaccine.

First of all, it was necessary to create an injector such that it would permit the vial of vaccine, after having been placed in it, to be kept in the refrigerator during the time when the injector was not being used. A simplistic solution for this injector would be to design it so that the whole apparatus could be kept in the refrigerator, and be removed only when there was need to apply an injection. However, this solution is not practical, since however small it may be the apparatus would occupy considerable space in the refrigerator and would be ice-cold when was time to be used and thus highly uncomfortable for the operator.

Another solution, perhaps more adequate, would be to keep only the vial of vaccine in the refrigerator and place it in the injector only when it is used for an application, after which the vial would be removed from the injector and put in the refrigerator again. Nevertheless, each time the vial is removed a little air would enter the vaccine circulation ducts, and for this to be avoided, the design of the injector would be quite complex and the cost too high.

The solution to the problems previously described was to create a vaccine suction and injection assembly that could be quickly separated from the main body of the injector without any entrance of air into the vaccine circulation ducts. Thus only the vaccine suction and injection system, including the vial, would be placed in the refrigerator. The main body of the injector would be kept outside, at room temperature. When preparing to use the apparatus, the operator would get the suction and injection assembly from the refrigerator, with the vial of vaccine duly in place, and would insert this assembly, by an operation taking only a moment, in the hydraulic energy storage assembly that constitutes the main body of the apparatus.

Therefore, the primary object of the present invention is to provide an injector in which it is possible to separate quickly and then reunite the vaccine system to the hydraulic system, and in which the air-tight seal of these two systems is perfectly maintained in the course of this operation.

This and further objects and advantages of the invention will become more apparent upon reference to the following specification, claims and drawing wherein;

Figure 1:
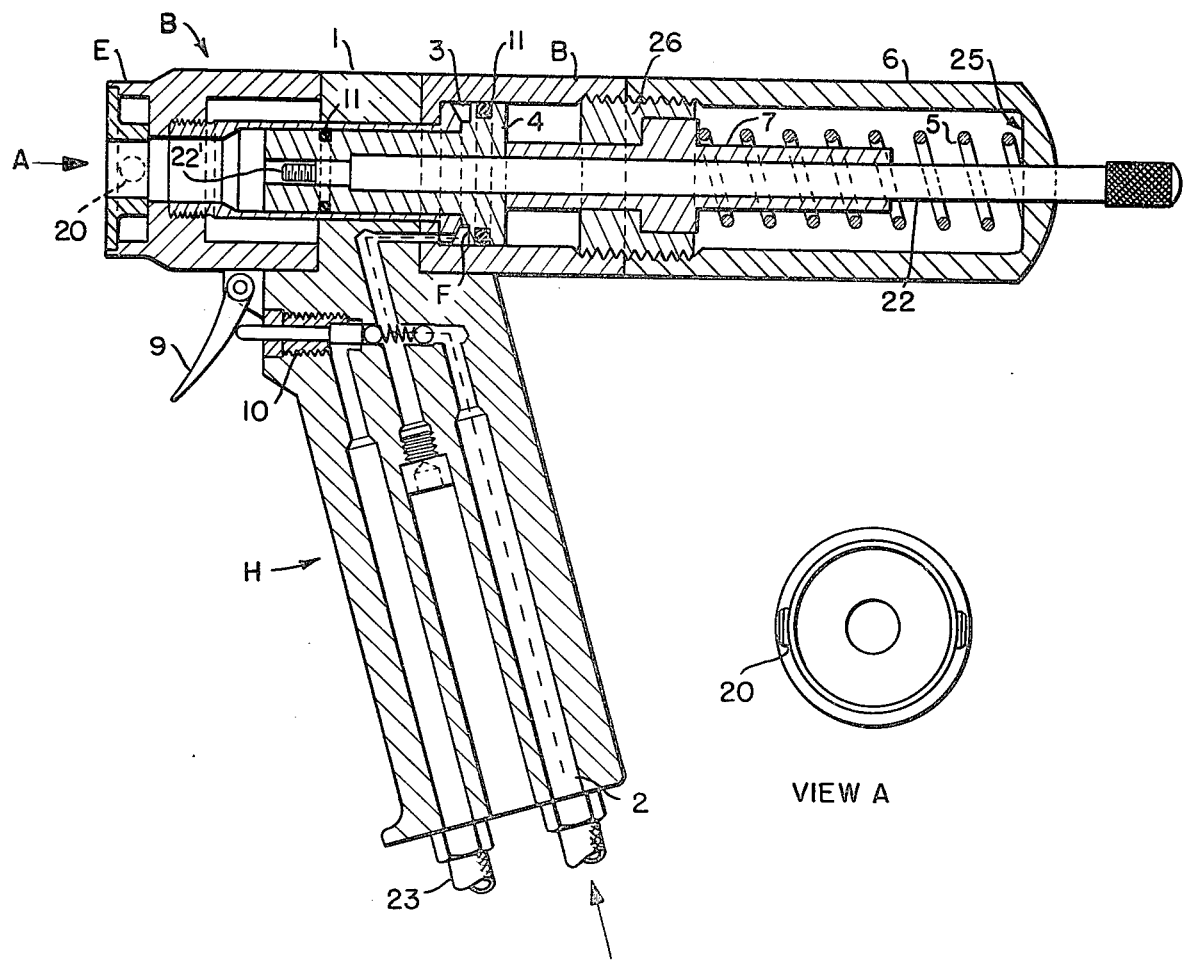
FIG. 1 is a side elevation, in cross-section of the hydraulic assembly of the injector for intermittent vaccination.

The functioning of the hydraulic assembly H of this injector is basically the same as that of other injectors intended for mass vaccination. The arrow in FIG. 1 indicates the entrance for hydraulic oil in the body of the pistol-grip 1 through the channel 2. This oil should be pumped by a hydraulic pump (not shown) capable of producing up to 3000 PSI (210 kg/cm$^2$) of pressure. It may be activated electrically or mechanically by means of a pedal. The volume of oil that penetrates into the grip is retained by a retention valve and accumulated in the pressure chamber 3 of the barrel B, forcing the hydraulic piston 4 rearwardly and compressing the piston rod 7 against the master spring 5. The rearward displacement of the hydraulic piston is equivalent to the distance between the rear end of the piston rod 7 and the stop 25 of the dosage cartridge barrel 6. That is, when the dosage cartridge is connected to the barrel B of the injector by means of the threaded fitting 26, the travel of the piston rod 7 will be limited by the stop 25 when the piston 4 is pushed rearwardly by the oil under pressure entering chamber 3. Thus, within the limits of its maximum displacement, the stroke of the piston 4 may be infinitely varied, depending on the length of the piston rod 7 in the interior of the dosage cartridge that is connected to the barrel B of the injector. It should be noted, meanwhile, that although the stroke of the piston may be varied, the compression placed upon the master spring 5 does not vary, since independently of the dosage cartridge which is connected to the injector, the distance between the face F of the piston rod 7 and the stop 25 is always the same when the piston is in its maximum withdrawn position. This guarantees that the energy stored in every spring will also be constant, for whatever dosage cartridge is being used.

When pressure is applied to the trigger 9 of the discharge valve 10, a passage is opened for escape of the oil retained in the pressure chamber 3 between the two sealing rings 11. By virtue of the energy stored in the compressed spring 5, the hydraulic piston 4 is forced violently forward, whereupon all the oil returns to the hydraulic pump by the exit hose 23. This closes a complete cycle of operation of the hydraulic assembly of the apparatus.

Figure 2:
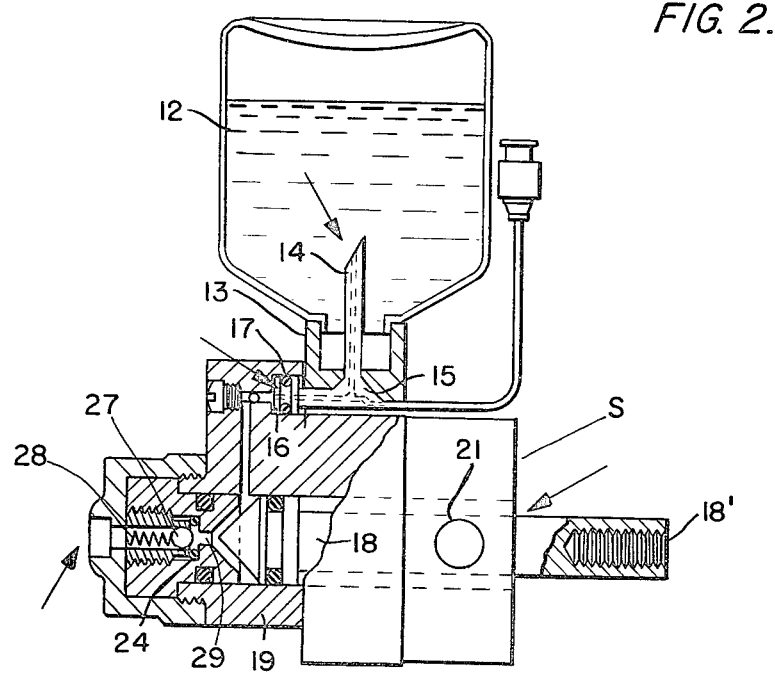
FIG. 2 is a side elevation, partly in section, of the vaccine suction and injection assembly of the injector for intermittent vaccination.

FIG. 2 shows the vaccine suction and injection assembly which constitutes the front part of the injector. It may be noted that the vial of vaccine 12 is placed "head down" or inverted in the vial support 13. When this vial is placed in the support, a point 14 of the needle cannula 15 goes through the rubber plug that seals the vaccine vial and penetrates into the interior, entering into direct contact with the immunizing liquid. For this reason it is desirable to sterilize this needle point periodically when the vial of vaccine is changed, although it is not necessary to so so every time.

Since the point of the cannula is very fine, and once placed in the holder the vial will remain there until all the contents are used, the elastic rubber plug of the vial forms a perfect seal around the needle, preventing any leakage of the vaccine. Obviously, if the same vial were removed and replaced several times in the holder, the rubber plug would be full of holes and the seal would not be so perfect. Besides, as has already been noted, every time the vial is removed from the holder a little air enters the needle, and the operator it obliged to waste the first shots so as to remove this air from the system, under the previous technique.

The great advantage of the system provided by the present invention lies in the fact that once the vial is placed in the support, the whole system remains hermetically sealed, thus differing substantially from other injectors where a seal exists only when the vaccine suction and injection system is mounted on the hydraulic part of the apparatus. Even during the rapid operation of coupling and uncoupling from the hydraulic part, the vaccine system of the injector for intermittent vaccination remains hermetically sealed, thus preventing that entrance of air which is so prejudicial to proper functioning of the apparatus. This arrangement is detailed in the following paragraphs.

In FIG. 2 four arrows may be noted, indicating four specific points in the vaccine suction and injection system. These are the four critical points with regard to entrance of air into the system. The first point 14 itself, where the vaccine is aspirated. Naturally the air can enter here only if the vial is removed from the holder, and since this does not occur in the present system, the seal is maintained until the whole vial is completely empty.

Another point that is usually quite critical as regards entrance of air is the union between and barrel of the needle and the vaccine entrance valve 16. This union, in other injectors, is made of steel to steel, has here been replaced by a rubber O-ring 17, making the seal much more efficient. Even after removal of the vial the needle remains firmly fixed to the entrance valve, something that does not occur with other hypodermic injectors.

The third place where air might enter is the very orifice by which the jet of vaccine is expelled. In other hypodermic injectors the seal at this point is accomplished by a nylon sphere 27 that is pushed by a small spring 28 against a spherical steel seat, this combination constituting the vaccination exit valve 29. In the injector for intermittent vaccination according to the present invention, this spherical seat is replaced by a rubber O-ring 24 which, in contact with the nylon sphere forms a seal at low pressure that is much more efficient than that of other hypodermic injectors.

Finally there is the last and most problematical point where air might enter, which is the back part of the vaccine suction and injection system, where the latter is coupled to the hydraulic system.

In other injectors the vaccine piston 18 is screwed manually to the hydraulic piston 4 and then the vaccine cylinder 19 is pushed against the piston and then fixed to the grip by a threaded retention ring. This operation, besides leaving the interior of the vaccine cylinder completely exposed to the air, is relatively time-consuming, requiring about two minutes. That is, every time the vaccine suction and injection system is disconnected from the hydraulic system it is necessary to sterilize it completely and then remove the air from its interior by successive shots. Taken all together, this sequence of operations takes more than five minutes of the vaccinator's time.

In the present invention, the vaccine suction and injection system is connected to the hydraulic system by means of two diametrically opposite self-retracting spring urged pins 20 in end E of barrel B which fit into two holes 21, also diametrically opposite one another, located in a sleeve S in the back part of the vaccine system when the barrel is fitted over the end E of sleeve B of the hydraulic assembly H. The vaccine piston 18 is fixed to the hydraulic piston 4 by means of a mandrel 22 that has one of its ends knurled, located at the back end of the dosage cartridge 6. When this knurled end is turned to the right, the threaded front part 22' of the mandrel 22 screws into the threaded bore 18' of the vaccine piston 18, holding it against the hydraulic piston 4. Thus any movement of the hydraulic piston is accompanied by movement of the vaccine piston, so that the latter performs the functions of sucking and injecting the immunizing liquid.

Therefore, to connect the vaccine system to the hydraulic system all that is necessary is to press the self-retracting pins, insert the vaccine system, and turn the rear knurled end, so as to fix the vaccine piston to the hydraulic system, and the injector will be ready for use, without entrance of air into either system. They are separated in the same way, by inverting or reversing the operation. According to experiments that have been made, the time necessary to join or separate the two systems is less than 10 seconds—much less than the time necessary to prepare a disposable syringe.

This invention further permits the use of a single body with the hydraulic assembly for series of assemblies for application of vaccine, which may contain vaccines of different types. These would be kept in the refrigerator until needed for application, while the body with the hydraulic system and energy storage may be kept at room temperature.

I claim:

1. In a hydraulic pressure actuated hypodermic injector for intermittent vaccination the combination comprising, a first part in the general shape of a postol including a hand grip and a barrel, a hydraulic assembly for storage of energy housed within said first part, a pressure chamber within said hydraulic assembly, valve means controlling hydraulic pressure within the pressure chamber, a second part comprising a vaccine suction and injection assembly, means on each of said parts whereby they may be quickly connected and disconnected one from the other without entrance of air into either of the two assemblies particularly into the ducts and places where vaccine is circulated and stored.

2. A hypodermic injector according to claim 1 wherein, a dosage cartridge is connected to the rear of said barrel, said dosage cartridge comprising a piston rod and a master spring, a hydraulic piston disposed within said barrel and urged by said spring toward said vaccine assembly, said spring having a predetermined initial compression, said dosage cartridge being removable from and connected to said barrel by a simple rotation thereof, wherein the initial compression of the said spring is never affected and said dosage cartridge can be quickly replaced by another one having another piston rod and another spring, said spring having a different initial compression and urging said hydraulic piston toward said vaccine assembly in a different displacement, thus permitting the required change in the dosage of the vaccine.

3. A hypodermic injector according to claim 1 wherein, said barrel includes diametrically opposed self-retracting pins spring urged outwardly from the outer surface of its front end, said suction and injection assembly including a sleeve at one end and a discharge valve at its other end, said sleeve being of larger diameter than the front end of said barrel portion and having a pair of diametrically opposed openings therein, a vaccine piston extending through said sleeve and having an internally threaded end, a mandrel rotatably mounted in said barrel and extending through said hydraulic piston, the end of the mandrel adjacent the front end of said barrel having external threads thereon, whereby when said sleeve is slid over the front and open end of said barrel the threaded ends of said vaccine piston and said mandrel are aligned and connected one to the other by rotation of said mandrel and the self-retracting pins on the open end of said barrel engage in the openings in said sleeve and connect said first and second parts together.

4. A hypodermic injector according to claim 3 wherein, said vaccine suction and injection assembly includes a vaccine entrance valve and a needle for carrying the vaccine connected to one another by an O-ring.

5. A hypodermic injector according to claim 3 wherein, said vaccine suction and injection assembly includes a vaccine exit valve which is sealed by means of a nylon sphere and an O-ring.

* * * * *

UNITED STATES PATENT AND TRADEMARK OFFICE
CERTIFICATE OF CORRECTION

PATENT NO. : 4,266,541

DATED : May 12, 1981

INVENTOR(S) : Sergio Landau

It is certified that error appears in the above-identified patent and that said Letters Patent are hereby corrected as shown below:

On the title page

-- [30] Foreign Application Priority Date
September 19, 1978 [BR] Brazil.........PI 7806153 --.

Col. 5 line 11, "postol" should read -- pistol --.

Signed and Sealed this

Thirty-first Day of August 1982

[SEAL]

Attest:

GERALD J. MOSSINGHOFF

Attesting Officer

Commissioner of Patents and Trademarks